(12) United States Patent
Blachechen et al.

(10) Patent No.: US 12,083,208 B2
(45) Date of Patent: Sep. 10, 2024

(54) CLEANSING COMPOSITIONS

(71) Applicant: Johnson & Johnson Consumer Inc., Skillman, NJ (US)

(72) Inventors: Tatiana Blachechen, Sao Jose dos Campos (BR); Maria Cristina Guedes Jorge, Sao Jose dos Campos (BR); Jacqueline Morais, Sao Jose dos Campos (BR); Christina Bishop, Clifton, NJ (US); Marni Dexter, Cranford, NJ (US)

(73) Assignee: Johnson & Johnson Consumer Inc., Skillman, NJ (US)

(*) Notice: Subject to any disclaimer, the term of this patent is extended or adjusted under 35 U.S.C. 154(b) by 344 days.

(21) Appl. No.: 15/971,098

(22) Filed: May 4, 2018

(65) Prior Publication Data

US 2018/0318195 A1   Nov. 8, 2018

Related U.S. Application Data

(60) Provisional application No. 62/501,213, filed on May 4, 2017.

(51) Int. Cl.
*A61K 8/46* (2006.01)
*A61K 8/36* (2006.01)
*A61K 8/37* (2006.01)
*A61K 8/41* (2006.01)
*A61K 8/44* (2006.01)
*A61K 8/60* (2006.01)
*A61K 8/86* (2006.01)
*A61Q 5/02* (2006.01)
*A61Q 5/12* (2006.01)
*A61Q 19/10* (2006.01)

(52) U.S. Cl.
CPC .......... *A61K 8/466* (2013.01); *A61K 8/361* (2013.01); *A61K 8/375* (2013.01); *A61K 8/416* (2013.01); *A61K 8/44* (2013.01); *A61K 8/602* (2013.01); *A61K 8/604* (2013.01); *A61K 8/86* (2013.01); *A61Q 5/02* (2013.01); *A61Q 5/12* (2013.01); *A61Q 19/10* (2013.01); *A61K 2800/30* (2013.01); *A61K 2800/48* (2013.01); *A61K 2800/596* (2013.01)

(58) Field of Classification Search
None
See application file for complete search history.

(56) References Cited

U.S. PATENT DOCUMENTS 3,590,122 A * 6/1971 Roberts et al. ........ A61K 8/361
424/70.19
5,478,490 A * 12/1995 Russo ...................... A61K 8/39
424/70.12
6,525,034 B2 * 2/2003 Dalrymple ............... A61K 8/42
514/613
2013/0143784 A1 6/2013 Rizk
2016/0095804 A1 4/2016 Xavier

FOREIGN PATENT DOCUMENTS

| CN | 104825344 A * | 8/2015 | |
| CN | 106232098 A | 12/2016 | |
| CN | 106176270 B * | 10/2017 | |
| DE | 102006034533 A1 * | 1/2008 | ............... A61K 8/42 |
| EP | 2532343 A1 | 12/2002 | |
| RU | 2282435 C2 | 5/2005 | |
| RU | 2535010 C2 | 5/2013 | |
| WO | WO 2016/147196 A1 | 9/2016 | |
| WO | WO 2017/140799 A1 | 8/2017 | |
| WO | WO 2017/140802 A1 | 8/2017 | |

OTHER PUBLICATIONS

SpecialChem (https://cosmetics.specialchem.com/inci/peg-80-sorbitan-laurate, no pagination (Year: 2015).*
Toxicology in Vitro, 13(2); 231-239, Apr. 1999.
Database GNPD [Online] MINTEL. Jul. 1, 2017—Pick n Pay: "Tear Free Baby Shampoo". XP002783434.
Database GNPD [Online] MINTEL; Sep. 1, 2015 (Sep. 1, 2015), Umberto Giannini : "Rebuild Strengthening Damage Repair Shampoo", XP002783429, Database accession No. 3430291 the whole document.
Database GNPD [Online] MINTEL; Feb. 1, 2016 (Feb. 1, 2016), Bumble and bumble: "Sul fate free Shampoo", XP002783430 Database accession No. 3741013 the whole document.
Database GNPD [Online] MINTEL; Feb. 1, 2017 (Feb. 1, 2017), Etude: "Soft Body Wash", XP002783431, Database accession No. 4630385 the whole document.
Database GNPD [Online] MINTEL; Sep. 1, 2013 (Sep. 1, 2013), Johnson & Johnson: "Cleanser", XP002783432, Database accession No. 2175412 the whoe document.
Database GNPD [Online] MINTEL ; Apr. 1, 2015 (Apr. 1, 2015), Master Line do Brasil : "Children shampoo", XP002783433, Database accession No. 3086677 the whoe document.
Stepan Company: "Stepan Sul fate-Free Cross Reference for Personal Care" May 25, 2015 (May 25, 2015), XP055495494, Retrieved from the Internet: URL:https://www.stepan.com/uploadedFi l es/Lit-erature and Downloads/General Lit/PersonalCare/StepanSulfateFreeCrossReferenceFor Personal Care.pdf [retrieved on Jul. 26, 2018] p. 3.
International Search Report for PCT/US2018/031041 dated Aug. 1, 2018.

* cited by examiner

*Primary Examiner* — Erin E Hirt
(74) *Attorney, Agent, or Firm* — Rachel Chaves

(57) ABSTRACT

Sulfate-free cleansing compositions that include a surfactant and a conditioning agent are disclosed. The cleansing compositions are suitably thick and have a desired level of clarity. The cleansing compositions, which are slightly acidic, are mild to the skin and/or eyes.

7 Claims, 2 Drawing Sheets

CLEANSING COMPOSITIONS

This application claims priority of the benefit of the filing of U.S. Provisional Application Ser. No. 62/501,213, filed May 4, 2017, the contents of which are hereby incorporated by reference in their entirety.

FIELD

The present invention is directed to sulfate-free cleansing compositions that include a surfactant and a conditioning agent. The cleansing compositions are suitably thick and have a desired level of clarity. The cleansing compositions, which are slightly acidic, are mild to the skin and/or eyes.

BACKGROUND

A number of different components are useful in performing the cleansing function of cleansing compositions. Surfactants are a class of useful components. Some surfactants are potentially irritating and would not by themselves be suitable in mild cleansing compositions.

Despite the potential irritating effects of certain surfactants in their pure or concentrated form, surfactant systems can be designed to be mild for skin and eyes by modifying the composition. Modifications include, for example, adding less irritating surfactants to the composition and/or diluting the amount of surfactant in the composition. It is important, however, that the cleansing composition still provide adequate cleansing and optionally conditioning benefits, particularly in a shampoo.

Compositions containing low levels of surfactants and/or less irritating surfactants usually require the use of thickeners to build viscosity in the composition. The use of thickeners, however, presents technical challenges to keep a clear appearance when cationic conditioning agents are employed. As a result, the compositions appear hazy or creamy. The situation becomes more challenging when the composition is free of surfactants containing sulfate groups, since the use of sulfate-free surfactants typically make it more difficult to thicken the final composition.

The present invention is a cleansing composition that includes a sulfate-free surfactant that provides a number of benefits desired by consumers. Such benefits include mildness, cleansing and/or conditioning performance, high clarity appearance, adequate viscosity and slightly acidic pH.

SUMMARY

The present invention is directed to a cleansing composition that contains:
- a surfactant system comprising at least one non-ionic surfactant, one amphoteric surfactant, and two anionic surfactants, wherein one of the anionic surfactants is an isethionate;
- a conditioning agent;
- a preservative system; and
- a thickener.

The cleansing composition may have a skin mildness score of IL-1, a release less than about 300 µg/ml, a pH of from about 3.5 to about 5.5, and a viscosity of about 1,000-9,000 cps at 25° C. using a Brookfield Viscometer, LV at 6 rpm. Other surfactants may be substituted or added, as described below.

DETAILED DESCRIPTION

Figure 1:
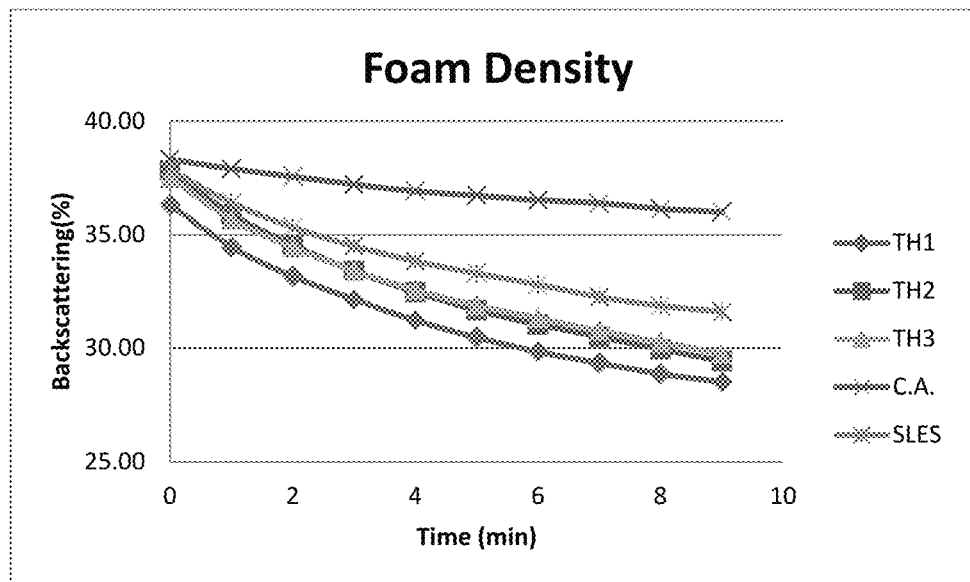
FIG. 1 is a graph showing foam density for, TH1, TH2 and TH3, which are samples prepared in accordance with the invention compared to SLSS as defined herein and a commercially available competitor formulation.

As used herein, the term "cleansing composition" (or alternatively "cleanser") refers to a flowable composition that is useful in cleansing dirt and/or oil from the skin or hair of the user. The cleansing composition is intended to be applied to the skin and/or hair of the user for a limited period of time and then removed by way of washing or wiping with a wipe or other tool.

As used herein with respect to the cleansing composition or its components, the term "sulfate-free" refers to a composition that does not include a component having a sulfate group. If the composition described herein is a "sulfate-free" composition (or a composition that is "free of sulfates"), the resulting composition lacks any component that has a sulfate group.

All percentages of components herein are in weight percentage. In some aspects, the percentage is the weight percent of the final cleansing composition, and in some aspects, the weight percentage is of the particular system being described. For example, the final cleansing composition desirably includes a surfactant system, which is a blend of a plurality of surfactants. Amounts of these surfactants may be described as being the weight percentage of the final cleansing composition or alternatively the weight percentage of the surfactant system, as noted in the description. If a component is described herein as being present in a particular weight percent with no further identifier, it is intended that the weight percent is with respect to the final cleansing composition.

The present inventors sought to prepare a cleansing composition that would be mild, thick, and clear, and still provide suitable cleansing and conditioning benefit to the skin or hair of a user. In particular, it was desired to prepare a cleansing composition that could be used on the skin or hair of a younger person, including babies, toddlers, and children. As such, it was desired that the composition have a slightly acidic pH, such as from about 3.5-5.5, or from about 4.5-5.5, when used. To achieve a desired pH level, one or more pH modifiers or adjusters may be used in the composition. Suitable pH adjusters include, for example, acids such as citric acids.

The composition desirably is mild to the skin and eyes. Mildness is defined herein as the ability of a product to be applied to the skin or hair of a user with a low or negligible level of irritation. Skin and/or eye mildness of the composition of the invention may be determined using one or more of the tests described below:

EpiDerm™ Skin Model

The EpiDerm™ (MatTek Corporation, Ashland, MA) is an in vitro model system for chemical, pharmaceutical and skin care product testing.

Using the EpiDerm™ Skin Kit (MatTek Corporation, Ashland, MA), solutions containing tissue are stored at 2-8° C. until use.

The day before treatment, the EpiDerm™ tissues are cultured in six-well plates containing a hydrocortisone free-assay medium (HCF-AM) and equilibrated at 37±1° C. in a humidified atmosphere of 5±1% $CO_2$ in air (standard culture conditions) overnight.

Each EpiDerm™ tissue is considered an independent sample. At least 16 hours after initiating the tissue cultures, the medium is removed from under the tissues and 0.9 ml of fresh, pre-warmed HCF-AM is added to each well. Each test article (100 µl) is applied onto three tissues, and the negative control (100 µl sterile, deionized H2O) is added to the other three tissues in the six-well plate. At the end of the 1-hour exposure period, each tissue is rinsed five times with approximately 0.5 ml per rinse of calcium- and magnesium-free Dulbecco's phosphate-buffered saline (CMF-DPBS) (Quality Biological). After rinsing, each tissue is placed in the designated well of a new six-well plate containing 0.9 ml of fresh HCF-AM and incubated at standard culture conditions for the post-exposure incubation period (24 hours).

Viability Assay

Tissue viability may be determined using a method based on the reduction of the yellow tetrazolium salt 3-(4,5-dimethylthiazol-2-yl)-2,5-diphenyltetrazolium bromide (MTT) to the purple formazan dye by mitochondrial succinate dehydrogenase in viable cells. A 1.0-mg/ml solution of MTT in warm MTT addition medium is prepared no more than 2 hours before use.

Upon the completion of the 24-hour post-exposure incubation, the tissues are removed from their incubation medium, rinsed with CMF-DPBS, blotted dry and transferred into pre-labelled 24-well plates containing 300 µl MTT solution per well. The medium remaining from under each tissue is quick-frozen (< or =−60° C.) for subsequent cytokine analysis.

After 3±0.1 hours of incubation in MTT, the EpiDerm™ tissues prepared as described above are blotted on absorbent paper and transferred into 24-well plates containing 2.0 ml of isopropanol per well and shaken at room temperature. After 2 hours, the absorbance of a 200-µl aliquot of tissue extract is measured at 550 nm (Molecular Devices VMax® Kinetic ELISA microplate reader, Sunnyvale, CA, USA). The viability of the tissues exposed to the test articles is calculated and expressed as a percentage relative to the viability of the negative control-treated tissues. The tissue viability value is taken as the mean value from the three independent wells tested in each experiment.

Preferably, the skin mildness scores of the compositions and methods of this invention should be MTT cell viability greater than 80%.

IL-1α Immunoassay

IL-1α is a cytokine of the interleukin 1 family that is responsible for the production of inflammation. It is produced mainly by activated macrophages, as well as neutrophils, epithelial cells, and endothelial cells. It plays an essential role in maintenance of skin barrier function. In vitro models can be used to determine the mildness or irritation potential of personal care products. Bernhofera et al., IL-1α and IL-1ra secretion from epidermal equivalents and the prediction of the irritation potential of mild soap and surfactant-based consumer products, Toxicology in Vitro, 13(2); 231-239, April 1999.

IL-1α concentration is determined using a kit from R&D Systems (Minneapolis, MN, USA) according to the manufacturer's instructions for Epiderm. Thawed media samples, collected as described previously, are tested neat and as 1:10 dilutions to keep the readings within the linear range of the assay. The IL-1α value reported for each test was the mean value from the three independent tissues used per test article in each experiment and plated in duplicate.

Preferably, the skin mildness scores of the compositions and methods of this invention should be IL-1α release less than about 300 µg/ml, more preferably IL-1α release less than about 250 pg/ml, more preferably IL-1α release less than about 200 pg/ml and most preferably IL-1α release less than about 150 pg/ml.

EpiOcular™ Test

EpiOcular™ is an in vitro test for the ocular safety of raw ingredients and final formulations. It has been used for many years by industry as a non-animal, in vitro alternative to assess the mildness of materials contacting the eyes.

Using the EpiOcular™ Human Cell Construct Kit (MatTek Corporation, Ashland, MA), solutions containing human cell constructs are stored at 2-8° C. until used. On the day of dosing, EpiOcular™ Assay Medium is warmed to approximately 37° C. Nine-tenths mL of Assay Medium are aliquoted into the appropriate wells of 6-well plates. The six-well plates are labeled to indicate test article and exposure time. The constructs are inspected for air bubbles between the agarose gel and cell culture insert prior to opening the sealed package. Cultures with air bubbles covering greater than 50% of the cell culture area are not used. The 24-well shipping containers are removed from the plastic bag and their surfaces were disinfected with 70% ethanol. The EpiOcular™ human cell constructs are transferred aseptically into the 6-well plates. The constructs are then incubated at 37±1° C. in a humidified atmosphere of 5±1% $CO_2$ in air (standard culture conditions) for at least one hour. The medium is then aspirated and 0.9 mL of fresh Assay Medium is added to each assay well below the EpiOcular™ human cell construct. The plates are returned to the incubator until treatment was initiated.

The test articles are administered to the test system as 3% w/v dilutions in sterile, deionized water (positive and negative control, 1.0% Triton®-X-100 and Johnson's® Baby Shampoo, respectively, are administered to the test system as 10% w/v dilutions in sterile, deionized water). Each test article dilution is prepared by weighing the test article into a prelabeled conical tube. Sterile, deionized water is added until a 3% w/v or 10% w/v dilution was achieved and the tube is vortexed prior to application. For the remainder of this report, each test article dilution is referred to as the test article.

Johnson's® Baby Shampoo has the following ingredients:
fragrance; polyquaternium-10; PEG-80 sorbitan laurate; glycerin; PEG-150 distearate; water; sodium trideceth sulfate; tetrasodium EDTA; cocamidopropyl betaine; sodium benzoate; ethylhexylglycerin; phenoxyethanol; potassium acrylates copolymer; citric acid; Yellow 6; Yellow 10; sodium hydroxide.

The EpiOcular™ cultures are treated in duplicate with the test articles at specific exposure times (from 0.33 up to 16 hours, four time points each). One hundred microliters of each test article is applied to each EpiOcular™ human cell construct. Duplicate cultures of the negative control (exposure time control), 100 µL of sterile, deionized water (Quality Biological, Inc., Gaithersburg, MD), are exposed for 0.25, 4, 8, and 24 hours. Duplicate cultures of the positive control, 100 µL of 0.3% Triton®-X-100 (Fisher), are exposed for 15 and 45 minutes. The exposed cultures are then incubated for the appropriate amount of time at standard culture conditions. After the appropriate exposure time, the EpiOcular™ cultures are extensively rinsed with Calcium and Magnesium-Free Dulbecco's Phosphate Buffered Saline (Ca++Mg++Free-DPBS) and the wash medium was decanted. After rinsing, the tissue is transferred to 5 mL of Assay Medium for a 10 to 20 minute soak at room temperature to remove any test article absorbed into the tissue. A 1.0 mg/mL solution of MTT in warm MTT Addition Medium is prepared no more than 2 hours before use.

Three-tenths mL of MTT solution are added to designated wells in a prelabeled 24-well plate. The EpiOcular™ constructs are transferred to the appropriate wells after rinsing with Ca++Mg++Free-DPBS. The trays are incubated for approximately three hours at standard culture conditions. After the incubation period with MTT solution, the EpiOcular™ cultures are blotted on absorbent paper, cleared of excess liquid, and transferred to a prelabeled 24-well plate containing 2.0 mL of isopropanol in each designated well. The plates are sealed with parafilm and stored in the refrigerator (2-8° C.) until the last exposure time is harvested. The plates are then shaken for at least two hours at room temperature. At the end of the extraction period, the liquid within the cell culture inserts is decanted into the well from which the cell culture insert was taken. The extract solution is mixed and 200 μL are transferred to the appropriate wells of a 96-well plate. Two hundred microliters of isopropanol are added to the two wells designated as the blanks. The absorbance at 550 nm (OD550) of each well is measured with a Molecular Devices Vmax plate reader.

The raw absorbance values is captured. The mean OD550 of the blank wells is calculated. The corrected mean OD550 values of the negative controls is determined by subtracting the mean OD550 value of the blank wells from their mean OD550 values. The corrected OD550 values of the individual test article exposure times and the positive control exposure times is determined by subtracting the mean OD550 value of the blank wells from their OD550 values. All calculations are performed using an Excel spreadsheet. The percent of control calculations can be made. Exposure time response curves are plotted with the % of Control on the ordinate and the test article or positive control exposure time on the abscissa. ET50 is used for the exposure time required to produce a defined effect when a test population is exposed to a fixed concentration or specified dose of a toxicant. The ET50 value is interpolated from each plot. To determine the ET50, two consecutive points are selected, where one exposure time resulted in a relative survival greater than 50%, and one exposure time resulted in less than 50% survival. Two select points are used to determine the slope and the y-intercept for the equation y=m(x)+b. Finally, to determine the ET50, the equation is solved for y=50. When all of the exposure time points showed greater than 50% survival, the ET50 value is presented as greater than the longest test article exposure time Skin mildness of the compositions of this invention may be measured using the EpiDerm™-ET50 test. This test consists of the determination of the pH of the neat liquid test article if possible (and/or dosing solution as appropriate) and a definitive assay to determine the ET50 (the exposure time which reduces MTT reduction by 50%). The toxicity of the test article is evaluated on the basis of the relative tissue viability versus exposure time. Viability will be determined by the NAD(P)H-dependent microsomal enzyme reduction of MTT (and to a lesser extent, by the succinate dehydrogenase reduction of MTT) in control and test article-treated cultures. Data are presented in the form of relative survival (relative MTT conversion) versus exposure time. Preferably, the skin mildness scores of the compositions and methods of this invention should be greater than about 10 hours, more preferably greater than about 15 hours and most preferably greater than about 20 hours.

Eye mildness of the compositions of this invention may be measured using the EpiOcular™ET50 test. This test consists of a determination of the direct MTT reduction potential and pH of the neat liquid test article if possible (and/or dosing solution as appropriate) and a single definitive assay. The toxicity of the test article will be evaluated by the exposure time required to reduce tissue viability to 50% of controls (ET50). Viability will be determined by the NAD(P)H-dependent microsomal enzyme reduction of MTT (and to a lesser extent, by the succinate dehydrogenase reduction of MTT) in control and test article-treated cultures. Data will be presented in the form of relative survival (relative MTT conversion) versus test article exposure time. Preferably, the eye mildness scores of the compositions and methods of this invention should be greater than about 10 hours more preferably greater than about 14 hours and most preferably greater than about 15 hours.

In another aspect, skin mildness of the compositions of this invention may be measured using the IL-1α Immunoassay described above.

Viscosity

The composition should have a particular viscosity to allow for flowability and usability when dispensed from a dispenser and applied onto the skin and/or hair of a user. The viscosity of the composition can be determined by Zero-Shear Viscosity Test: Determinations of zero-shear apparent viscosity of the cleansing compositions were conducted on a controlled-stress rheometer (AR-2000™, TA Instruments Ltd., New Castle, Del., USA). Steady-state shear stress sweeps were performed at 25.0±0.1° C. using a cone-plate geometry. Data acquisition and analysis were performed with the Rheology Advantage software v4.1.10 (TA Instruments Ltd., New Castle, Del., USA). Zero-shear apparent viscosities for Newtonian fluids are reported as the average of viscosity values obtained over a range of shear stresses (0.02-1.0 Pa). For pseudoplastic (shear-thinning) fluids, zero-shear apparent viscosities were calculated via the fitting of shear stress sweep data to an Ellis viscosity model. Except otherwise stated, viscosities are given in centiPoise (cps).

In some aspects, the composition of the present invention may have a viscosity of from about 1,000-9,000 cps at LV#2, 6 rpm at 25° C. In other aspects, the viscosity may be from about 2,500 to about 5,000 cps at LV#2, 6 rpm at 25° C. In yet other aspects, the viscosity may be from about 1,000 to about 9,000 cps at LV#2, 3 rpm at 25° C.

The composition is desirably clear. As used herein, clarity refers to the composition having a light transmittance of greater than about 90%, more preferably greater than about 90.5%, and most preferably greater than about 95% as determined by the Clarity Test as described below. As used herein, the term "clear composition" shall mean that the composition shall have a count rate of less than about 70 kcts/s, more preferably less than about 50 kcts/s, and most preferably less than about 40 kcts/s, as determined by the Light Scattering Test as described below One method to determine the clarity is by measuring the capacity of light to cross the sample with minimum interaction, such as reflection, refraction and absorption, which decreases the light intensity relative to the source. The greater the clarity, the lower the interaction between the sample and light. As such, clear composition transmittance results in higher than 40.000 as measured by UV spectroscopy at 800 nm (wavelength) and glass cuvette with 10 cm of cell path.

Alternatively, clarity may be measured via the Clarity Test and/or Light Scattering Test as follows:

Clarity Test

The clarity test procedure comprises preparing a 1 cm cell sample of the composition to be measured and measuring the % light transmittance associated with such sample using an Agilent 8453 UV-Visible Spectrophotometer, Agilent Technologies, Santa Clara, CA, with a 1 cm cell at a wavelength of 800 nm. The clarity can be determined for each cleansing composition without dilution. The results are reported as % T, the % transmittance through the cleansing composition in the 1 cm cell.

Light Scattering Test

The clarity of a cleanser is determined by colloidal assembles that scatter light. A cleanser that is clearer typically will have only small colloidal assemblies. Larger colloidal assemblies, on the order of ⅓ the wavelength of light, will scatter light and produce a hazy or turbid solution.

The cleanser samples were analyzed using a Zetasizer Nano ZS DLS instrument (Malvern Instruments, Inc., Southborough, Mass.) operating at 25.0° C. The instrument was integrated with the Malvern Dispersion Technology Software. The unfiltered sample solutions were diluted to 3% and dispensed into cuvettes (12 mm Square Polystyrene Cuvettes, DTS0012) to the 10 mm mark, and covered. The measurements were done at attenuation 7, with a 4 mW He—Ne, 633 nm laser at position 4.65 mm. The temperature was kept constant at 25° Celsius. Measurements were done in 3 repetitions and 11 runs each.

The laser (at 633 nm) is incident on the cleansing composition and scatters from colloidal assemblies back to the detector. A hazy cleansing solution will have more and larger colloidal particles therefore producing more scattering to the detector and a higher count rate.

The composition may optionally be foamable, which means that the composition is capable of forming a foam during application to the hair or skin in contact with water. The composition desirably is slightly acidic, e.g., having a pH of between about 3.5 to about 5.5, or from about 4.0 to about 5.0. Cleansers having a pH below about 5.5 are beneficial to support the skin's natural acid mantle.

It is desirable to incorporate a surfactant system into the cleansing composition, to achieve desired cleansing of the user's skin and/or hair. Anionic surfactants are desired for this purpose. However, it is desired to avoid the use of sulfate-containing surfactants. As such, sulfate-free anionic surfactants have a tendency to provide a hazy composition, which has a lower degree of clarity. In addition, non-sulfate anionic surfactants show a tendency to be more difficult to thicken in a composition, requiring the use of additional thickeners. As will be described below, the addition of thickeners also reduces the level of clarity in the final composition. This lack of clarity typically results in such compositions being sold in opaque packages. While that may be sufficient for certain uses, it is desired that the composition of the present invention be clear. In some aspects, the composition of the present invention may be packaged and sold in transparent or translucent packages. In addition to the surfactant system, the invention desirably also includes a conditioning agent(s).

The problem with achieving the right balance of clarity, viscosity and mildness in a sulfate-free surfactant system, which still provides sufficient cleansing, is noteworthy. Adding one component may thicken the solution and provide the desired viscosity, but may reduce clarity. Reducing the surfactant level or other components may aid in the clarity, but may reduce cleansing effectiveness. In other scenarios increasing the surfactant level can solubilize other component and lead to increased clarity, but create a system that is no longer mild to the skin and or eye. In some aspects, including a conditioning agent is desired, but may reduce the clarity associated with the resulting composition. As will be described in greater detail below and with reference to the Examples, the present inventors have discovered a composition that meets all criteria and still provides a desired cleansing product.

The composition may include one or more thickeners in addition to the polyquaternium agent, however, it was discovered that a number of thickeners were found to result in compositions that were undesirably hazy, and therefore the viscosity was not at a desirable level. It was found that this issue could be overcome by modifying the pH to a more neutral level (e.g., about 7), however, the composition of the present invention desirably includes a pH that is slightly acidic, e.g., about 3.5-5.5 or about 4.0 to about 5.0. By contrast, in order to achieve a desirably viscous composition without a thickener, the inventors found that additional surfactants can be included in the composition. However, higher surfactant amount results in decrease in mildness.

Therefore, the problem to be solved by the present invention is providing a sulfate-free cleansing composition that includes a desirable surfactant system, conditioning agent, and thickener, while maintaining a suitable skin and/or eye mildness levels as described above, a slightly acidic pH, a viscosity level as described above, and clarity as measured by UV spectroscopy at 800 nm (wavelength) and glass cuvette with 10 cm of cell path. As will be discussed in the Examples, the present invention overcomes the issues of the prior art through a unique and surprising blend of surfactants and other components.

Surfactant System

The present invention includes a surfactant system, which includes at least one anionic surfactant, one nonionic surfactant and one amphoteric surfactant. The surfactant system may include more than one of each type of surfactant, more than two of each type of surfactants, more than three surfactants, or more than four surfactants. In one embodiment, the surfactant system includes five surfactants. It is desirable that a surfactant system including a blend of surfactants provide suitable cleansing and ultimately, when combined with other components, provide a suitable cleansing composition that fulfills the properties desired and explained above. The surfactant system may be present in an amount of about 5% to about 15% by weight of the final cleansing composition, or about 7.5% to about 12.5% by weight of the cleansing composition, or about 9% to about 11% by weight of the cleansing composition.

The surfactant system may include a combination of anionic, nonionic and amphoteric surfactants in a ratio of from about 1:2:2 to about 1:2:3. In some aspects, the combination of first anionic surfactant (e.g., an isethionate) and second anionic surfactant (e.g., a taurate or sulfosuccinate) is present in a ratio of from about 1:1 to about 5:1, or alternatively that the first anionic surfactant is present in a lower amount than the second anionic surfactant. In this aspect or alternatively, the combination of non-ionic surfactants (e.g., a laurate and glucoside) may be present in a ratio of from about 1:1 to about 1:5, respectively. Alternatively, a glucoside may be present in an amount that is greater than twice the amount of the laurate.

In one aspect, the anionic surfactants in the surfactant blend are present in a combined amount of about 5-30% by weight of the surfactant blend, or about 15-25% by weight of the surfactant blend. The anionic surfactants may be present in an amount of about 0.2-5% by weight of the final composition or about 1-2.5% by weight of the composition. In one embodiment, the anionic surfactants used in the surfactant system includes a taurate or other sulfosuccinate as one of the anionic surfactants. The taurate or sulfosuccinate may be present in an amount of from about 10-80% by weight of the total anionic surfactant in the system, or about 15-60% by weight of the total anionic surfactants in the system. The taurate or sulfocuccinate may be present in an amount of about 0.02-4% or about 0.15-1.5% by weight of the final cleansing composition. One exemplary taurate is sodium methyl cocoyl taurate. Additional taurates include, for example, Sodium Methyl Lauroyl Taurate, Sodium Methyl Miristoyl Taurate, Sodium Methyl Oleyl Taurate, Sodium Methyl Palmitoyl Taurate, Sodium Methyl Stearoyl Taurate, Sodium Methyl Miristoyl Taurate, Sodium Cocoyl Taurate, and Sodium Lauroyl Taurate. Suitable sulfosuccinates include, for example, Disodium Lauryl Sulfosuccinate, Disodium Laureth Sulfosuccinate Disodium C12-14 Pareth-1 Sulfosuccinate, Disodium C12-14 Pareth Sulfosuccinate, Disodium Cetearyl Sulfosuccinate, Disodium Cetyl Sulfosuccinate, Disodium Coco-Glucoside Sulfosuccinate, Disodium Coco-Sulfosuccinate, Disodium Cocoyl Butyl Gluceth-10 Sulfosuccinate, Disodium Stearyl Sulfosuccinate and Disodium Tridecylsulfosuccinate.

It was found that the surfactant system desirably includes another anionic surfactant different from the anionic surfactant described above, where this other anionic surfactant includes an isethionate. The presence of the isethionate was surprisingly found to provide additional clarity to the composition, as will be seen in the Examples below. The isethionate may be present in an amount of from about 30-95% by weight of the total anionic surfactants in the system, or about 40-85% by weight of the total anionic surfactants in the system. The isethionate may be present in an amount of about 0.06-4.8% or about 0.4-2.25% by weight of the final cleansing composition. One exemplary isethionate useful in the invention is sodium cocoyl isethionate. Other suitable isethionates include, for example, Sodium Hydrogenated Cocoyl Methyl Isethionate, Sodium Isethionate, Sodium Lauroyl Methyl Isethionate, Sodium Lauroyl Isethionate, Sodium Myristoyl Isethionate, Sodium Myristoyl Isethionate, Sodium Oleoyl Isethionate, Sodium Oleyl Methyl Isethionate, Sodium Palm Kerneloyl Isethionate, and Sodium Stearoyl Methyl Isethionate The surfactant system desirably also includes at least one amphoteric surfactant in the surfactant system. The total amount of amphoteric surfactants may be present in an amount of about 25%-70% by weight of all surfactants in the surfactant system, or about 35-50% by weight of the total surfactants in the surfactant system. The amphoteric surfactant may be present in an amount of about 1.2-10.5% or about 2.5-5.0% by weight of the final cleansing composition. Suitable amphoteric surfactants include, for example, betaines, such as cocoamidopropyl betaine.

The surfactant system desirably also includes at least one non-ionic surfactant in the surfactant system. The total amount of non-ionic surfactants may be present in an amount of about 20%-60% by weight of all surfactants in the surfactant system, or about 35-45% by weight of the total surfactants in the surfactant system. Non-ionic surfactants useful in the surfactant system include, for example, laurates, such as PEG-80 sorbitan laurate, and glucosides such as decyl glucoside or cocoglucoside. The surfactant system may include a first non-ionic surfactant and a second non-ionic surfactant, where the first and second non-ionic surfactants are different from each other.

In some aspects, the first non-ionic surfactant may include a polyoxyethylene derivative of polyol esters, wherein the polyoxyethylene derivative of polyol ester is derived from (a) a fatty acid containing from about 10 to about 18, and preferably from about 12 to about 14 carbon atoms, and (b) a polyol selected from sorbitol and sorbitan. The polyoxyethylene derivative of polyol ester may contain an average of from about 10 to about 120, and preferably about 20 to about 80 oxyethylene units. Further, the polyoxyethylene derivative of polyol ester may have an average of about 1 to about 3 fatty acid residues per mole of polyoxyethylene derivative of polyol ester. Examples of such polyoxyethylene derivatives of polyol esters include, but are not limited to PEG-80 sorbitan laurate and Polysorbate 20. PEG-80 sorbitan laurate, which is a sorbitan monoester of lauric acid ethoxylated with an average of about 80 moles of ethylene oxide, is available commercially from Croda (East Yorkshire, UK) under the tradename, "Tween 28." Polysorbate 20, which is the laurate monoester of a mixture of sorbitol and sorbitol anhydrides condensed with approximately 20 moles of ethylene oxide, is available commercially from Croda (East Yorkshire, UK) under the tradename "Tween 20." In some aspects, the glucoside may be a linear alkyl glucoside.

As noted above, there may be one non-ionic surfactant in the cleansing composition, or alternatively, the non-ionic surfactant includes a combination of at least a first non-ionic surfactant and a second non-ionic surfactant. The first non-ionic surfactant may be present in an amount of about 10-60% by weight of the surfactant system, or about 15-50% by weight of the surfactant system. The second non-ionic surfactant may be present in an amount of about 20-95% by weight of the surfactant system, or about 50-85% by weight of the surfactant system. The first non-ionic surfactant may be present in an amount of about 0.1-6% by weight of the cleansing composition, or about 0.3-2.5% by weight of the cleansing composition. The second non-ionic surfactant may be present in an amount of about 0.2-9.5% by weight of the cleansing composition, or about 1.2-4.25% by weight of the cleansing composition. The first non-ionic surfactant may include, for example, a laurate, and the second non-ionic surfactant may include, for example, a glucoside.

Conditioning Agent

As discussed above, the desired composition may include one or more conditioning agents, such that the system is useful for cleansing and conditioning purposes. Conditioning agents are known and provide usefulness to cleansing compositions, however, it was discovered that the combination of certain conditioning agents with thickeners resulted in an undesirable lack of clarity.

It is desired to use a polyquaternium conditioning agent in the cleansing composition. Despite the above-mentioned clarity issue, the present inventors have found that polyquaternium agents are preferred over other agents, such as chloride phosphates and adipates, since such other conditioning agents often require higher amounts to provide the same or comparable benefits as polyquaternium agents. Suitable polyquaternium agents include, for example, Polyquaternium-67, Polyquaternium-10, Polyquaternium-7, Polyquaternium-4, Polyquaternium-5, Polyquaternium-6, Polyquaternium-7, Polyquaternium-22, Polyquaternium-47, Polyquaternium-39, and Polyquaternium-53. Polyquaternium-10 is the preferred conditioning agent, but others are contemplated. In some aspects, the composition includes only one conditioning agent, and in such embodiments, the only one conditioning agent may be polyquaternium-10. Polyquaternium agents may be included in an amount of from about 0.05% to about 0.5%, and more desirably from about 0.1% to about 0.3% by weight of the final composition.

In addition to the polyquaternium agent(s), it may be useful to incorporate glycerin into the conditioning agent system. Glycerin is an optional component and may be included in an amount of about 0% (if no glycerin is used) or from about 0.1% to about 6% by weight of the final composition, or from about 0.5% to about 1.0% by weight of the final composition. In some aspects, a conditioning system providing a creamy feel may be desired, and in these embodiments, it may be desirable to include smooth conditioning agents such as hydroxypropyl guar and/or hydroxypropyltrimonium chloride, where the smooth conditioning agent is present in an amount from 0% (if no smooth conditioning agent is used) or from about 0.1% to about 1.0% by weight of the final composition, or about 0.15% to about 0.5% by weight of the final composition. Other components in the conditioning agent system that may be used include, for example, Hydroxypropyl Guar Hydroxypropyltrimonium Chloride, Polyquaternium-67, Polyquaternium-10, Polyquaternium-7, Polyquaternium-4, Polyquaternium-5, Polyquaternium-6, Polyquaternium-7, Polyquaternium-22, Polyquaternium-47, Polyquaternium-39, Polyquaternium-53, and PEG-12 Dimethicone.

In some aspects, it is desired to have a "high conditioning" system in the final cleansing composition, while in others, it is desired to have a "low conditioning" system in the final cleansing composition. It is understood that these are relative terms, and refer to the amount of conditioning agent(s) with respect to each other. In one example, a low conditioning system may include a polyquaternium compound (e.g., PQ-10) in an amount of about 0.15% by weight of the final composition, and may include glycerin or glycerin substitutes in an amount of about 0.50% by weight of the final composition. In another example, a high conditioning system may include a polyquaternium compound (e.g., PQ-10) in an amount of about 0.20% by weight of the final composition, and may include glycerin or glycerin substitutes in an amount of about 1.0% by weight of the final composition. If desired, either the low conditioning system or the high conditioning system may further include one or more creamy conditioning agents, as described above.

Thickener

As noted above, the desirable composition provides a particular viscosity when dispensed from a dispenser and applied onto the skin and/or hair of a user. In some aspects, the composition of the present invention may have a viscosity of from about 1,000-9,000 cps at LV#2, 6 rpm at 25° C., or alternatively at 3 rpm at 25° C. In other aspects, the viscosity may be from about 2,500 to about 5,000 cps at LV#2, 6 rpm at 25° C. To achieve the desired thickness, various thickeners were attempted but many resulted in lack of clarity or other defects as explained above.

The thickeners useful in the present invention include polyethylene glycols, such as PEG-150 distearate, which is a polyethylene glycol diester of stearic acid, sometimes referred to as polyethylene glycol 6000 distearate or polyoxyethylene (150) distearate. Other polyethylene glycols include, for example, PEG-120 Methyl Glucose Dioleate, PEG-18 Glyceryl Oleate/Cocoate, PEG-55 Propylene Glycol Oleate, PEG-200 Hydrogenated Glyceryl Palmate; and PEG-7 Glyceryl Cocoate. Thickeners may be included in any desired amount, such that they provide the desired viscosity levels but bearing in mind that the clarity and mildness levels described above should still be achieved. Thickeners may be used in amounts of from about 0.01% to about 4% by weight of the final composition, or alternatively about 0.01% to about 1.5% by weight of the final composition.

pH Adjuster

As noted above, the final composition desirably is slightly acidic. To achieve this result, it may be desired to include one or more pH adjusters. Acids may be included in the composition, including, for example, citric acid. Other useful acidic components include, for example, lactic acid, glycolic acid, and salicylic acid. pH adjusters may be included in any desired amount to achieve the desired pH level, including for example, from about 0.1% to about 1.0% by weight of the final composition, or from about 0.25% to about 0.5% by weight of the final composition. In some aspects, more pH adjuster may be needed, while in others, less of a pH adjuster may be required. It may be possible that no pH adjuster is required, although it is useful to incorporate a pH adjuster to achieve the specifically desired level of acidity.

Preservatives

Preservatives may be included to provide shelf life and longevity of the product. By way of example, preservative systems may include, for example, sodium benzoate, Benzoic Acid, Sorbic Acid and its salts, Dehydroacetic Acid and its Salts, Phenoxyethanol, Caprylyl Glycol, Chlorphenesin, and Ethylhexylglycerin. The preservative system may be included in any desired amount, such as from about 0.1% to about 1.0% by weight of the final composition, or about 0.5% by weight of the final composition.

Other Components

The composition may include water or other aqueous carrier in an amount of about 60% to about 90% by weight of the final composition, or about 70% to about 85% by weight of the final composition.

It may be desired to include one or more chelating agents, such as ethylenediaminetetraacetic acid (EDTA) disodium. Other chelating agents useful in the composition include, for example, ethylenediaminetetraacetic acid (EDTA) tetrasodium and Tetrasodium Glutamate Diacetate. Chelating agents may be used in an amount of from about 0.001% to about 0.25% by weight of the final composition, or from about 0.01% to about 0.15% by weight of the final composition.

Some compositions may include optional components such as fragrances, colorants, and other aesthetic components. If used, fragrances and colorants may be present in a combined amount of from about 0.01% to about 6% by weight of the composition. Colorants may be less desirable to achieve a fully clear composition, but may be included provided that the final composition meets the definition of clarity defined above.

Opacifying Agent

In some aspects of the invention, the composition described above may be an intermediate composition, to which a further opacifying agent may be added. The addition of an opacifying agent may be helpful to provide a milky and/or creamy look to the composition, however, it is understood that the composition prior to adding the opacifying agent should desirably have the attributes described above, including thickness and clarity. Opacifying/pearlescent agents may include such additives as Glycol distearate, Ethylene Glycol Distearate, Glycol Monostearate, Styrene/Acrylates Copolymer, Stearic acid and its salts and Alkanolamides higher fatty acids.

Package

The cleansing composition described in this application may be included in any type of package desired, including, for example, pump-style packages, squeeze bottles or tubes, and the like. It may be desired that the package be transparent or translucent, such that the clarity of the composition may be viewed by a user at the time of purchase.

Method of Use

The product may be applied to the skin or hair of a user in any desired fashion. In some aspects, the product may be applied directly by hand, or a device such as a washcloth, sponge or other apparatus may be used to apply product. The composition is desirably applied to wet hair or skin so as to aid in the application. The composition may be left to sit on the applied area for a desired level of time, such as from about 5 seconds to about 5 minutes, and then washed with water to remove from the applied area.

EXAMPLES

As noted above, the present inventors have discovered that a sulfate-free, surfactant based cleansing composition may be achieved, while meeting the criteria for mildness, clarity, thickness, and acidity. As will be described below, the inventors underwent a significant number of tests, noting that while adding a component to a composition may aid in one criterion, it typically failed in another criterion. Of particular difficulty was achieving the blend of clarity and thickness, and therefore it is particularly desired to have a cleansing composition that meets the aforementioned clarity and thickness criteria.

Initial Surfactant Blend

The first composition developed included a blend of surfactants, each of which were sulfate-free, including a betaine (cocoamidopropyl betaine), a laurate (PEG-80 sorbitan laurate), a glucoside (decyl glucoside), and a taurate (sodium methyl cocoyl taurate). Sodium benzoate was added as a preservative in an amount of 0.5% by weight of the final composition. The taurate was present in an amount of 2.16% by weight of the composition, the betaine in an amount of 11.5% by weight of the composition, the laurate in an amount of 4.5% by weight of the composition, and the glucoside present in an amount of 4.2% by weight of the composition. In addition to the surfactant blend, the composition also included glycerin in an amount of about 1%, citric acid qs for pH 4.0-5.0, and water qs 100%.

In order to provide hair cleansing and conditioning effects, it was desired to include not only the surfactants but also a conditioning agent. To achieve this, the conditioning agent polyquaternium 10 (in an amount of 0.2% by weight of the composition) was added. However, the resulting system was found to be clear, but too liquidy (Composition C1). To attempt to provide a more clear composition while also thickening the composition, several thickeners were tested, including versathix (PEG-150 Pentaerythrityl Tetrastearate (and) PPG-2 Hydroxyethyl Cocamide), Carbopol EDT 2020 (Acrylates/C10-30 alkyl acrylate crosspolymer), Carbopol Aqua SF2 (Acrylates Crosspolymer-4), glucomate DOE-120 (PEG-120 Methyl Glucose Dioleate), and PEG-150 distearate, and none of them was found to provide a clear and viscous composition. The thickeners were tested in varying amounts of from 1% to 3% by weight of the final composition.

TABLE 1

Comparison of Thickener Agents: Comparative Examples (C1-C7)

| | INCI name | C1 % | C2 % | C3 % | C4 % | C5 % | C6 % | C7 % |
|---|---|---|---|---|---|---|---|---|
| Anionic | Sodium Methyl Cocoyl Taurate | 0.52 | 0.52 | 0.52 | 0.52 | 0.52 | 0.52 | 0.52 |
| Amphoteric | Cocamidopropyl Betaine | 4.37 | 4.37 | 4.37 | 4.37 | 4.37 | 4.37 | 4.37 |
| Non-ionic | PEG-80 Sorbitan Laurate | 3.24 | 3.24 | 3.24 | 3.24 | 3.24 | 3.24 | 3.24 |
| Non-ionic | Decyl Glucoside | 2.1 | 2.1 | 2.1 | 2.1 | 2.1 | 2.1 | 2.1 |
| | Sodium Benzoate | 0.5 | 0.5 | 0.5 | 0.5 | 0.5 | 0.5 | 0.5 |
| | Polyquaternium-10 | 0.2 | 0.2 | 0.2 | 0.2 | 0.2 | 0.2 | 0.2 |
| | Glycerin | 1.0 | 1.0 | 1.0 | 1.0 | 1.0 | 1.0 | 1.0 |
| | Citric Acid | | | | qs pH 4.5 | | | |
| | Water | | | | qs 100% | | | |
| Thickener | Versathix (PEG-150 Pentaerythrityl Tetrastearate (and) PPG-2 Hydroxyethyl Cocamide) | | 1.4 | | | | | |
| | Glucamate DOE (PEG-120 Methyl Glucose Dioleate) | | | 1.5 | 3.0 | | | |
| | Carbopol Aqua SF-2 (Acrylates Crosspolymer-4) | | | | | 3.0 | | |
| | PEG-150 Distearate | | | | | | 1.0 | 2.0 |
| | Clarity | Clear | Slight Hazy | Hazy | Hazy | Opaque | Slight Hazy | Hazy |
| | Viscosity | Liquid | Liquid | Slight Viscous | Slight Viscous | Viscous | Slight viscous | Viscous |

While the resulting compositions (C2-C7) as shown in Table 1 appeared either viscous or slightly viscous, the majority showed either haziness or white coloring. PEG-150 distearate as a thickener in an amount of 1% by weight appeared slightly hazy, but properly viscous. Considering the tested thickeners, the PEG-150 distearate appeared to be the most promising thickener agent to provide a clear composition at pH below 5.0 with the conditioning agent.

The composition, however, remained unclear and the present applicants sought to modify the surfactant composition.

Increasing Anionic Surfactants

Although Applicants wished to modify the surfactant blend in the composition to have a higher anionic surfactant level, so as to solubilize the conditioning agent, it was important to maintain the total anionic surfactant concentration at a safe and desirable level such that the composition would still be considered mild under the test criteria described above. The four surfactants identified above were still included in a test composition, however, the relative ratios of the surfactants were modified. The anionic, amphoteric and non-ionic surfactants were tested in different weight ratios of: 20:40:40; 15:45:40; 20:50:30; 20:30:50. In each test, the non-ionic surfactants were a blend of 4 parts of PEG-80 Sorbitan Laurate and 1 part of Decyl Glucoside. In each tested composition, the preservative and conditioning agents were maintained at constant levels. See Table 2 below.

Substitution or Combination of Taurate

The inventors sought to test other anionic surfactants in addition to and in substitution for the taurate in the original surfactant blend, with the understanding that it was known that sulfate-free surfactants were notoriously difficult to thicken a composition. The inventors tested the composition described above, but substituting the taurate for: (a) isethionate only, (b) sulfosuccinate only, (c) a 1:1 weight ratio blend of taurate with isethionate and (d) a 1:1 weight ratio blend of taurate with sulfosuccinate. For the blended com-

TABLE 2

Increased Anionic Concentration Tested at Different Surfactants Balance: Comparative Examples (C8-C11)

| | INCI name | C8 20:40:40 ratio % | C9 15:45:40 ratio % | C10 20:50:30 ratio % | C11 20:30:50 ratio % |
|---|---|---|---|---|---|
| Anionic | Sodium Methyl Cocoyl Taurate | 2.2 | 1.6 | 2.2 | 2.2 |
| Amphoteric | Cocamidopropyl Betaine | 3.6 | 4.1 | 4.5 | 2.7 |
| Non-ionic | PEG-80 Sorbitan Laurate | 2.9 | 2.9 | 2.1 | 3.6 |
| Non-ionic | Decyl Glucoside | 0.7 | 0.7 | 0.5 | 0.9 |
| | Sodium Benzoate | 0.5 | 0.5 | 0.5 | 0.5 |
| | Polyquaternium-10 | 0.2 | 0.2 | 0.2 | 0.2 |
| | Glycerin | 1.0 | 1.0 | 1.0 | 1.0 |
| | Citric acid | qs pH 4.5 | qs pH 4.5 | qs pH 4.5 | qs pH 4.5 |
| | Water | qs | qs | qs | qs |
| | PEG-150 Distearate | 1.0 | 1.0 | 1.0 | 1.0 |
| | Clarity | Clear | Hazy | Slight Hazy | Clear |
| | Viscosity | Liquid | Viscous | Slight Viscous | Liquid |

Comparative examples (C9-C10) did not show clarity. Further, C8 and C11 with the ratio of 20:40:40 and 20:30:50 (anionic: amphoteric: non-ionic surfactants, by weight) appeared to exhibit some clarity but lacked sufficient viscosity. Therefore, there was still a need to improve the viscosity. Composition C8, with higher amphoteric surfactant content 20:40:40, showed to be easier to thicken.

positions (c) and (d), the thickener was used in an amount of 1.5% by weight, while in blended compositions (a) and (b), the thickener was used in the amount of 1.0% by weight. In each tested composition, the preservative and conditioning agents were maintained at constant levels. See Table 3 below.

TABLE 3

Substitution of or Combination with Taurate: Comparative Examples (C8; C12-C15)

| | INCI name | (C8) Only Taurate (%) | (C12) Only Isethionate (%) | (C13) Only Sulfosuccinate (%) | (C14) Taurate + Isethionate (%) | (C15) Taurate + Sulfosuccinate (%) |
|---|---|---|---|---|---|---|
| Anionic | Sodium Methyl Cocoyl Taurate | 2.2 | — | — | 1.1 | 1.1 |
| Anionic | Sodium Cocoyl Isethionate | — | 1.8 | — | 0.9 | — |
| Anionic | Disodium Lauryl Sulfosuccinate | — | — | 1.8 | — | 0.95 |
| Amphoteric | Cocamidopropyl Betaine | 3.6 | 3.6 | 3.6 | 3.6 | 3.6 |
| Non-ionic | PEG-80 Sorbitan Laurate | 2.9 | 2.9 | 2.9 | 2.9 | 2.9 |
| Non-ionic | Decyl Glucoside | 0.7 | 0.7 | 0.7 | 0.7 | 0.7 |
| | Sodium Benzoate | 0.5 | 0.5 | 0.5 | 0.5 | 0.5 |
| | Polyquaternium-10 | 0.2 | 0.2 | 0.2 | 0.2 | 0.2 |
| | Glycerin | 1.0 | 1.0 | 1.0 | 1.0 | 1.0 |
| | Citric acid | qs | qs | qs | qs | qs |
| | Water | qs | qs | qs | qs | qs |

TABLE 3-continued

Substitution of or Combination with Taurate: Comparative Examples (C8; C12-C15)

| INCI name | (C8) Only Taurate (%) | (C12) Only Isethionate (%) | (C13) Only Sulfosuccinate (%) | (C14) Taurate + Isethionate (%) | (C15) Taurate + Sulfosuccinate (%) |
|---|---|---|---|---|---|
| PEG-150 Distearate | 1.0 | 1.0 | 1.0 | 1.0 | 1.0 |
| Clarity | Clear | Hazy | Hazy | Clear | Hazy |
| Viscosity | Liquid | Viscous | Viscous | Slight Viscous | Viscous |

Comparative examples C12-C15 showed the substitution of or combination with isethionate and sulfosuccinate appeared to demonstrate better thickness when compared to C8, where taurate was the unique anionic surfactant, but the use of the taurate and isethionate provided the promise of a more clear and viscous composition. However, the composition still lacked the proper combination of desired attributes as defined above.

Modifying Proportion of Glucoside and Laurate

The inventors also considered a different modification to thicken the composition while improving its clarity, which was to modify the proportion between the non-ionic surfactants: Decyl glucoside and PEG-80 sorbitan laurate. The system tested was based on 9% active matter, balance of 20:40:40 anionic: amphoteric: non-ionic surfactant blend, which contained only the taurate (SCMT) as the anionic surfactant. In each tested composition, the preservative and conditioning agents were maintained at constant levels. See Table 4 below.

Based on comparative examples C8, C16-C19, the results described on Table 4, the decyl glucoside was found to help build formula viscosity, and PEG-80 sorbitan laurate appeared to have more profound influence on the clarity, where the composition with high Laurate content (C16) showed better clarity but poor viscosity, and the composition with higher Glucoside content (C19) showed sufficient viscosity, but lacked on clarity. The composition C18 was found to provide a good balance between clarity and viscosity.

Taurate Combination and Glucoside/Laurate Proportion

Taking into account the experimental results seen in the tests conducted with substitution of the taurate (Table 3), in combination with the results seen when the glucoside/laurate proportion was modified (Table 4), the inventors modified the initial surfactant composition to use the taurate substitution in addition to the glucoside/laurate proportion. In each tested composition, the preservative and conditioning agents were maintained at constant levels. See Table 5.

TABLE 4

Modifying Proportion of Non-ionic Surfactants: Comparative Examples (C16-C19)

| | INCI name | (C16) 0:5 Decyl:PEG80 SL (%) | (C8) 1:4 Decyl:PEG80 SL (%) | (C17) 1:1 Decyl:PEG80 SL (%) | (C18) 4:1 Decyl:PEG80 SL (%) | (C19) 5:0 Decyl:PEG80 SL (%) |
|---|---|---|---|---|---|---|
| Anionic | Sodium Methyl Cocoyl Taurate | 2.2 | 2.2 | 2.2 | 2.2 | 2.2 |
| Amphoteric | Cocamidopropyl Betaine | 3.6 | 3.6 | 3.6 | 3.6 | 3.6 |
| Non-ionic | PEG-80 Sorbitan Laurate | 3.6 | 2.9 | 1.8 | 0.7 | — |
| Non-ionic | Decyl Glucoside | — | 0.7 | 1.8 | 2.9 | 3.6 |
| | Sodium Benzoate | 0.5 | 0.5 | 0.5 | 0.5 | 0.5 |
| | Polyquaternium-10 | 0.2 | 0.2 | 0.2 | 0.2 | 0.2 |
| | Glycerin | 1.0 | 1.0 | 1.0 | 1.0 | 1.0 |
| | Citric acid | qs pH 4.5 | qs pH 4.5 | qs pH 4.5 | qs pH 4.5 | qs pH 4.5 |
| | Water | qs | qs | qs | qs | qs |
| | PEG-150 Distearate | 1.0 | 1.0 | 1.0 | 1.0 | 1.0 |
| | Clarity | Clear | Clear | Slight Clear | Slight Hazy | Slight Hazy |
| | Viscosity | Liquid | Liquid | Slight Viscous | Viscous | Viscous |

TABLE 5

Comparative (C18-C19) and Inventive Examples (I1-I2)

| | INCI name | (C18) 4:1 Decyl:PEG80 1:0 taur.:Isethi. (%) | (I1) 4:1 Decyl:PEG80 1:1 taur.:Isethi. (%) | (I2) 3:2 Decyl:PEG80 1:1 taur.:Isethi. (%) | (C19) 1:1 Decyl:PEG80 1:1 taur.:Isethi. (%) |
|---|---|---|---|---|---|
| Anionic | Sodium Methyl Cocoyl Taurate | 2.2 | 1.1 | 1.1 | 1.1 |
| Anionic | Sodium Cocoyl Isethionate | | 0.9 | 0.9 | 0.9 |
| Amphoteric | Cocamidopropyl Betaine | 3.6 | 3.6 | 3.6 | 3.6 |
| Non-ionic | PEG-80 Sorbitan Laurate | 0.7 | 0.7 | 1.4 | 1.8 |
| Non-ionic | Decyl Glucoside | 2.9 | 2.9 | 1.7 | 1.8 |
| | Sodium Benzoate | 0.5 | 0.5 | 0.5 | 0.5 |
| | Polyquaternium-10 | 0.2 | 0.2 | 0.2 | 0.2 |
| | Glycerin | 1.0 | 1.0 | 1.0 | 1.0 |
| | Citric acid | qs pH 4.5 | qs pH 4.5 | qs pH 4.5 | qs pH 4.5 |
| | Water | qs | qs | qs | qs |
| | PEG-150 Distearate | 1.0 | 1.0 | 1.0 | 1.0 |
| | Clarity | Slight Hazy | Clear | Cleary | Slight Clear |
| | Viscosity | Viscous | Viscous | Viscous | Viscous |

It was found that the combination of isethionate with taurate from Comparative Example C14, in addition to the glucoside/laurate proportion modification inspired in Comparative Example C18 provided the guidance to prepare compositions that were suitably viscous and clear: including Inventive Example I1 and I2.

Based upon the tests described on Table 3, it was determined that the combination of the taurate and the sulfocuccinate (either disodium lauryl sulfosuccinate or disodium laureth sulfosuccinate) did not provide a suitably clear and viscous composition. However, it was determined that the inclusion of the isethionate would be important in achieving a clear and viscous composition, while still achieving the mildness properties and cleansing efficiency described above.

The decyl glucoside used in the above examples could, however, be substituted with cocoglucoside as described in Inventive Example I3, and the sodium methyl cocoyl taurate could be substituted by either disodium lauryl sulfosuccinate (I4) or disodium laureth sulfosuccinate (I5). The invention could, therefore, include a surfactant blend of Sodium Cocoyl Isethionate and Sodium methyl cocoyl taurate, Sodium Cocoyl Isethionate and Disodium Lauryl Sulfosuccinate, or Sodium Cocoyl Isethionate and Disodium Laureth Sulfosuccinate.

The combination of isethionate and either a taurate or a second anionic surfactant can vary in proportion inside an acceptable range and provide viscous and clear composition as described in Inventive Example 16. Respecting the optimal balance between the surfactants, the total surfactant amount in the system may be reduced keeping the desired clarity and viscosity as showed in Inventive Example 17. The thickener PEG-150 distearate used in the above examples could, however, be substituted by PEG-200 Hydrogenated Glyceryl Palmate; PEG-7 Glyceryl Cocoate as described in Inventive Example 18 and provide viscous and clear composition.

TABLE 6

Inventive Examples (I3-I8)

| | INCI name | (I3) 4:1 Coco:PEG80 1:1 taur.:Isethi. (%) | (I4) 4:1 Decyl:PEG80 1:1 Sulfosuc.:Isethi. (%) | (I5) 4:1 Decyl:PEG80 1:1 Sulfosuc.:Isethi. (%) | (I6) 3:1 Decyl:PEG80 1:4 taur.:Isethi. (%) | (I7) 3:1 Decyl:PEG80 1:4 taur.:Isethi. (%) | (I8) 4:1 Decyl:PEG80 1:1 taur.:Isethi. (%) |
|---|---|---|---|---|---|---|---|
| Anionic | Sodium Methyl Cocoyl Taurate | 1.1 | | | 0.34 | 0.25 | 1.1 |
| Anionic | Sodium Cocoyl Isethionate | 0.9 | 0.9 | 0.9 | 1.32 | 1.15 | 0.9 |
| Anionic | Disodium Lauryl Sulfosuccinate | | 0.9 | | | | |
| Anionic | Disodium Laureth Sulfosuccinate | | | 0.9 | | | |
| Amphoteric | Cocamidopropyl Betaine | 3.6 | 3.6 | 3.6 | 3.9 | 3.42 | 3.6 |
| Non-ionic | PEG-80 Sorbitan Laurate | 0.7 | 0.7 | 0.7 | 0.81 | 0.70 | 0.7 |
| Non-ionic | Decyl Glucoside | | | | 2.56 | 2.25 | 2.9 |
| Non-ionic | Coco Glucoside | 2.9 | 2.9 | 2.9 | | | |
| | Sodium Benzoate | 0.5 | 0.5 | 0.5 | 0.5 | 0.5 | 0.5 |
| | Polyquaternium-10 | 0.15 | 0.15 | 0.15 | 0.2 | 0.2 | 0.2 |

TABLE 6-continued

Inventive Examples (I3-I8)

|  | INCI name | (I3)<br>4:1 Coco:PEG80<br>1:1 taur.:Isethi.<br>(%) | (I4)<br>4:1 Decyl:PEG80<br>1:1<br>Sulfosuc.:Isethi.<br>(%) | (I5)<br>4:1 Decyl:PEG80<br>1:1<br>Sulfosuc.:Isethi.<br>(%) | (I6)<br>3:1 Decyl:PEG80<br>1:4 taur.:Isethi.<br>(%) | (I7)<br>3:1 Decyl:PEG80<br>1:4 taur.:Isethi.<br>(%) | (I8)<br>4:1 Decyl:PEG80<br>1:1 taur.:Isethi.<br>(%) |
|---|---|---|---|---|---|---|---|
|  | Glycerin | 1.0 | 1.0 | 1.0 | 1.0 | 1.0 | 1.0 |
|  | Citric acid | qs pH 4.5 | qs pH 4.5 | qs pH 4.5 | qs pH 4.5 | qs pH 4.5 | qs pH 4.5 |
|  | Water | qs | qs | qs | qs | qs | qs |
| Thickener | PEG-150 Distearate | 0.25 | 0.30 | 0.30 | 0.65 | 0.75 |  |
| Thickener | PEG-200 Hydrogenated Glyceryl Palmate; PEG-7 Glyceryl Cocoate |  |  |  |  |  | 3.3 |
|  | Clarity | Clear >40.000 | Cleary >40.000 | Clear >40.000 | Clear >40.000 | Clear >40.000 | Clear >40.000 |
|  | Viscosity | Viscous (2489 cPs) | Viscous (4339 cPs) | Viscous (1555 cPs) | Viscous (3510 cPs) | Viscous (3180 cPs) | Viscous (5000 cPs) |
|  | Mildness Score | 169.31 | 186.32 | 137.50 | 91.81 | Not determined | Not determined |

Foaming Attributes

A foam evaluation test was conducted by inducing foam formation by a standard procedure and evaluating its characteristic using a light backscattering technique. The standard procedure for foam formation consists of transferring, volumetrically, 1 mL of a 0.5% test solution to a spectrophotometer tube and mixing for 2 minutes with a platform mixer set at 150 cycles/minute. Samples had been prepared with purified water at 0.5% m/v. Equipment used: Turbiscan™ Classic MA 2000 Stability Analyzer.

TH1; TH2; TH3; which are samples prepared in accordance with the invention, were compared to SLES (sodium lauryl ether sulfate used at 12.5% w/v as positive control); and a commercially available competitor shampoo formulation.

TH1, TH2 and TH3 have the following ingredients:

|  | TH1 | TH2 | TH3 |
|---|---|---|---|
| Decyl Glucoside | 5.12 | 5.12 | 5.76 |
| Polyquaternium-10 | 0.2 | 0.15 | 0.2 |
| Glycerin | 1 | 0.5 | 1 |
| Cocamidopropyl Betaine | 10.23 | 10.23 | 9.5 |
| Water | 77.83 | 78.38 | 74.81 |
| Disodium EDTA | 0.15 | 0.15 |  |
| Water; Sodium Methyl Cocoyl Taurate |  |  | 4.5 |
| Hydroxypropyl Guar Hydroxypropyltrimonium Chloride |  |  | 0.15 |
| Sodium Cocoyl Isethionate |  |  | 0.9 |
| Sodium Benzoate | 0.5 | 0.5 | 0.5 |
| PEG-150 Distearate | 0.6 | 0.6 | 0.65 |
| PEG-80 Sorbitan Laurate; Water | 1.13 | 1.13 | 1.03 |
| Glycol Distearate |  |  | 0.5 |
| Sodium Cocoyl Isethionate | 1.32 | 1.32 |  |
| Citric Acid | 0.5 | 0.5 | 0.5 |
| Sodium Methyl Cocoyl Taurate; Water | 1.42 | 1.42 |  |

Figure 2:
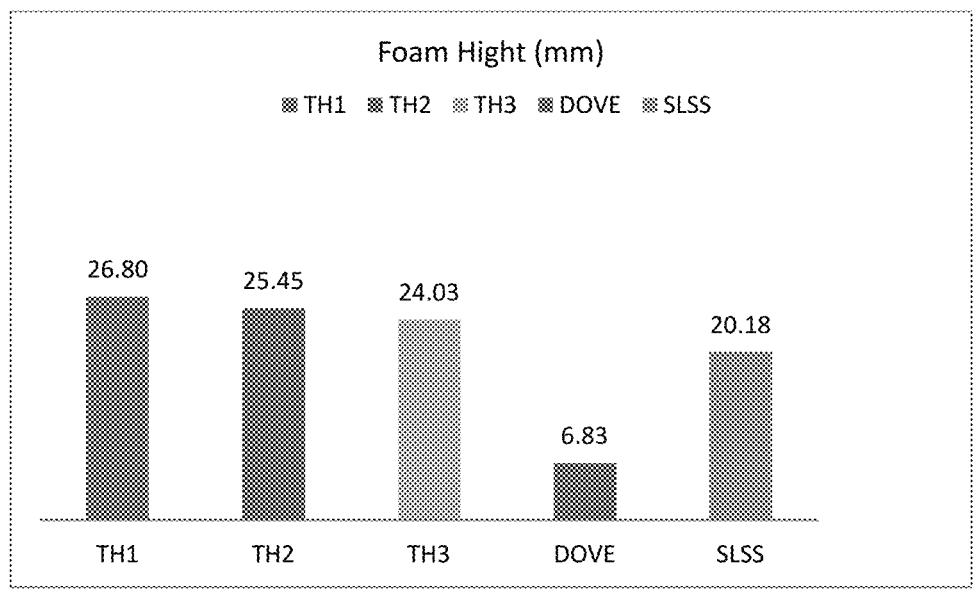
FIG. 2 is a graph showing foam height for, TH1, TH2 and TH3, which are samples prepared in accordance with the invention compared to SLSS as defined herein and a commercially available competitor formulation.

The commercially available competitor shampoo formulation has the following ingredients:

cocamidopropyl betaine, sodium cocoyl glycinate, polyacrylate-33, sodium lauryl isethionate, lauric acid, sodium hydroxide, styrene/acrylates copolymer, sodium tallowate, sodium isothionate, sodium stearate, sodium cocoate, sodium palm kernelate; glycerin, stearic acid, polyquartenium-10, dimethiconol, caprylyl glycol; phenoxyethanol, water, parfum, tetrasodium EDTA, and etidronic acid The results are shown in FIGS. 1 and 2. FIG. 1 is a graph showing foam density for, TH1, TH2 and TH3, which are samples prepared in accordance with the invention compared to SLES and a commercially available competitor shampoo formulation (C.A.). FIG. 2 is a graph showing foam height for, TH1, TH2 and TH3, which are samples prepared in accordance with the invention compared to SLES (SLSS in FIG. 2) and a commercially available competitor shampoo formulation.

Foam density is related to consumer perception, i.e., the higher the density, the higher the perception of creaminess. FIG. 1 shows that the compositions of the invention demonstrate good foam density even though they do not contain sulfate. FIG. 1 also shows that the compositions of the invention have good foam stability, i.e., the longer amount of time that the foam remains, the more stable.

Foam height is related to the ability to foam, i.e., the higher the height, the higher the ability of the system to foam. FIG. 2 shows that the compositions of the invention demonstrate good foam height even though they do not contain sulfate.

Summary of Experimental Results

As described above, the present inventors undertook significant experimental effort to achieve a composition that provided desired attributes, including foaming ability, clarity, viscosity, and/or mildness to the skin and/or eyes. The inventors began with a blend of surfactants that although originally were believed to provide a suitable composition, were determined not to meet desired attributes. The inventors discovered an acceptable blend of components that work together to form a desirable composition.

What is claimed is:

1. A cleansing composition comprising:
   a surfactant system comprising:
      a first non-ionic surfactant, wherein the first non-ionic surfactant is PEG-80 sorbitan laurate in an amount of about 0.5-2% by weight of the cleansing composition, a second non-ionic surfactant, wherein the second non-ionic surfactant is decyl glucoside in an amount of about 1% to about 5% by weight of the cleansing composition, an amphoteric surfactant comprising a betaine in an amount of about 1.2% to about 10.5% by weight of the cleansing composition, and a first anionic surfactant and a second anionic surfactant together in an amount of about 1% to about 2.5% by weight of the cleansing composition, wherein the first anionic surfactant is sodium methyl cocoyl taurate, wherein the second anionic surfactant is an isethionate present in an amount of less than 1.0% by weight of the cleansing composition, and wherein the first anionic surfactant and the second anionic surfactant are present in the cleansing composition a weight ratio of about 1:1;

a conditioning agent comprising a polyquaternium component present in an amount of about 0.1% to about 0.3% of the cleansing composition;

a preservative system present in an amount of about 0.5% by weight of the cleansing composition; and a thickener present in an amount of about 1% by weight of the cleansing composition, wherein the cleansing composition is free of a sulfate surfactants, and wherein the cleansing composition has a skin mildness score of IL-1α release less than about 150 pg/ml, a pH of from about 3.5 to about 5.5, and a viscosity of about 1,000-9,000 cps at 25° C.

2. The cleansing composition of claim 1, wherein the cleansing composition has a transmittance greater than 40.000 percent as measured by UV spectroscopy at 800 nm and glass cuvette with 10 cm of cell path.

3. The cleansing composition of claim 1, wherein the preservative system comprises sodium benzoate or benzoic acid.

4. The cleansing composition of claim 1, wherein the thickener is selected from the group consisting of PEG-150 distearate, PEG-200 hydrogenated glyceryl palmitate or PEG-7 glyceryl cocoate.

5. The cleansing composition of claim 1, wherein the cleansing composition comprises a pH adjuster.

6. The cleansing composition of claim 5, wherein the pH adjuster comprises an acid.

7. The cleansing composition of claim 1, wherein:
the PEG-80 sorbitan laurate is present in an amount of about 0.7% by weight of the cleansing composition, and the decyl glucoside is present in an amount of about 2.9% by weight of the cleansing composition.

* * * * *